United States Patent [19]

Clift

[11] Patent Number: 5,452,716
[45] Date of Patent: Sep. 26, 1995

[54] METHOD AND DEVICE FOR IN VIVO MEASURING THE CONCENTRATION OF A SUBSTANCE IN THE BLOOD

[75] Inventor: Vaughan Clift, Houston, Tex.

[73] Assignee: Novo Nordisk A/S, Bagsvaerd, Denmark

[21] Appl. No.: 126,247

[22] Filed: Sep. 24, 1993

Related U.S. Application Data

[63] Continuation-in-part of Ser. No. 836,284, Feb. 25, 1992, abandoned.

[51] Int. Cl.⁶ ................................................. A61B 5/00
[52] U.S. Cl. ........................................ 128/633; 356/39
[58] Field of Search ............................ 128/633–635, 128/664–667; 356/39–41

[56] References Cited

U.S. PATENT DOCUMENTS

| | | | |
|---|---|---|---|
| 4,169,676 | 10/1979 | Kaiser | 128/633 X |
| 4,427,889 | 1/1984 | Muller | 128/633 X |
| 4,655,225 | 4/1987 | Dahne et al. | 128/633 |
| 4,975,581 | 12/1990 | Robinson et al. | 128/633 X |
| 5,137,023 | 8/1992 | Mendelson et al. | 128/633 |
| 5,313,941 | 5/1994 | Braig et al. | 128/633 |

Primary Examiner—Angela D. Sykes
Attorney, Agent, or Firm—Steve T. Zelson; Elias J. Lambiris

[57] ABSTRACT

In vivo measurement of the concentration of a substance in the blood, e.g. glucose, despite varying concentrations of interfering components, e.g. protein and fat, by measuring the absorption of infra red light at a pair of selected wavelengths in the range 1–40 μm for each of the substance and the components one being a measuring wavelength at which the substance or component show a specific absorption and another being a reference wavelength at which the substance or component shows a low absorption, at least one wavelength being selected from the range 1–10 μm. The absorption is measured using a detector providing a computable electric signal corresponding to the absorbed amount of infra red radiation at the respective wavelengths. The electric signals are used to calculate the concentration of the substance taking into account the absorption caused by the interfering components.

29 Claims, 7 Drawing Sheets

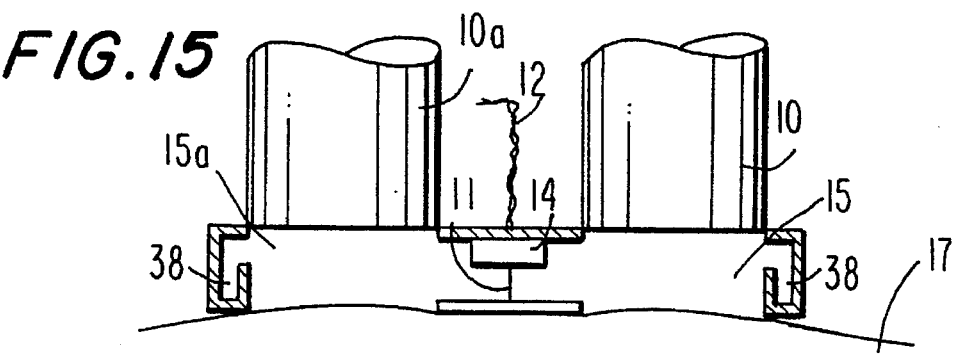
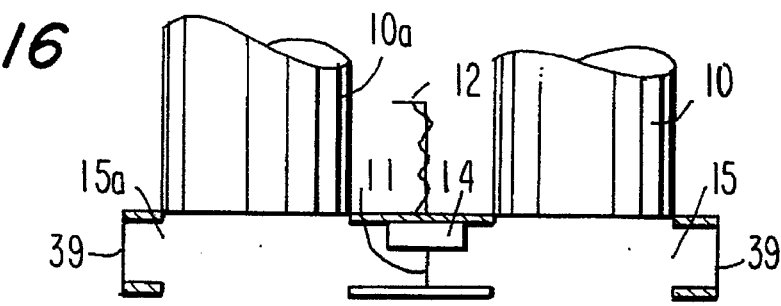
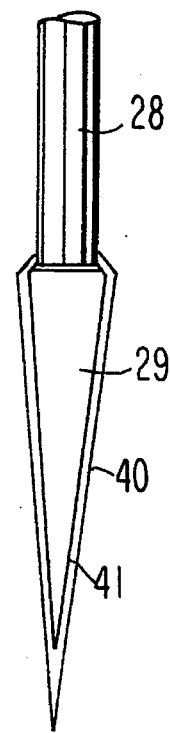
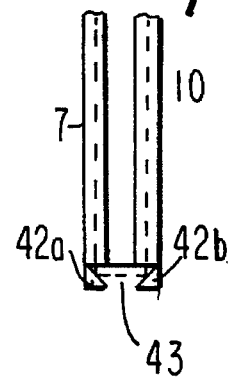

METHOD AND DEVICE FOR IN VIVO MEASURING THE CONCENTRATION OF A SUBSTANCE IN THE BLOOD

This application is a continuation-in-part of Ser. No. 07/836,284 filed Feb. 25, 1992 now abandoned, the contents of which are incorporated herein by reference.

The present invention concerns a method and a device for measuring in vivo the concentration of a substance, preferably sugar, despite of varying concentrations of interfering components, e.g. fat, protein and water in blood.

Continuous maintenance of normal blood sugar levels is important in avoiding the deterioration of a number of body organs. For example it is considered a prerequisite in prevention of the progression of diabetic microangiopathy in the kidney, the retina, and in autonomic and peripheral nerves. However, under normal conditions for managing a diabetic condition it is virtually impossible to maintain blood sugar concentrations continuously at normal levels. This is largely because the uptake of carbohydrates and conversion to glucose in the blood is not predictable. Blood sugar levels are normally determined by regular in vitro measurements and the quantity of insulin required to maintain normal blood sugar levels is based on predictions of glucose uptake and consumption during the period between measurements. Thus for example if diabetics find themselves in the position of engaging in unpredicted exercise especially after an injection of insulin, they can all too readily become comatose. Diabetes is hence very difficult to manage in children and adults. Also in the unwell or premature neonate reserves of glucose are limited and control mechanisms immature predisposing them to dangerously low blood sugar levels.

At present blood sugar levels are normally determined by regular in vitro measurements requiring puncturing the skin, taking away a blood sample and using an in vitro method which usually takes two minutes. This induces considerable restraint on taking blood sugar measurements. These constraints on measuring blood sugar levels and poor predictability of blood glucose levels have significant impact on the lifestyle of a diabetic patient and the well being of any seriously ill patient.

As a result of these difficulties in managing a diabetic condition there is a long standing need for a device that is capable of continuously measuring in vivo blood sugar levels. Such a device could be used for controlling the injection of insulin into the blood in response to increases in blood sugar levels. Such a device is known as an artificial pancreas. Attempts have been made to combine in vivo determination of blood sugar levels with an insulin pump controlled by a micro-computer. However, these have been a failure because the method of continuously monitoring blood sugar levels was not reliable. Attempts have been made to make continuous blood sugar measurement in vivo using presently available enzyme techniques such as glucose oxidase reduced onto an electrode. These devices comprise in general the coating of an anode with an enzyme specific for glucose, covering this with a glucose permeable membrane and measuring a small potential difference, or current, between this electrode inserted into a subcutaneous layer with another electrode. However, the method has proved unreliable because the currents and/or potentials are minute and subject to electrical noise, the membranes become coated by the body preventing the diffusion of glucose into the electrode and small molecules like uric acid, enzymes and other factors destroy the enzyme.

Optical methods have also been previously suggested for measuring the glucose molecule using its physical properties such as refractive index, ability to rotate the plane of polarized light and absorption in the infra-red spectrum, especially the near infra-red. For instance, in published Canadian Patent No. 1,247,397 there is disclosed an I.R. absorption method using discrete frequencies of near infra-red light and light transmitted or diffusely reflected from the irradiated tissue. The difficulty with such a method is discussed below.

Infrared spectroscopy has been proposed as an alternative to electrochemical techniques for continuously monitoring in vivo blood sugar levels. The problems associated with such a proposal are described in an article published in the International Journal of Artificial Organs, Vol. 12, No. 2 1988, pages 129 to 135 "Artificial Pancreas Blood Glucose Measured by Infrared Spectroscopy" by H. Zeller, P. Novak and R. Landgraf. The principal difficulty concerns the strong background absorption spectra of water and other blood constituents which make distinguishing the "fingerprint" of glucose difficult. This absorption is so strong as to effectively prevent any method using mid to far I.R. light transmitting the light through any volume of tissue.

Another difficulty in near I.R. is that the technique requires the maintenance of a fixed path length of sample through which the light passes. Also, the varying concentrations of the other components of blood which also absorb I.R. light produce significant error in measurement.

Until now research had concentrated on infra-red spectroscopy or photometric methods in the near infra-red as wavelengths of light in this region are capable of penetrating through flesh. However, wavelengths beyond this range have the advantage that absorption by the glucose molecule is stronger and more sharply delineated permitting it to be more readily differentiated from the other components of blood.

Attempts to use the near infra-red have largely been unsuccessful because of the limited absorption by the markedly attenuated glucose overtones in this region and the overlying spectra of numerous molecules including water. Also the systems previously described have had to maintain a fixed path length.

Other methods such as are disclosed in Swiss patent CH 612,271 have described the use of A.T.R. (Attenuated Total Reflection) prisms and the use of spectroscopy by means of a Fourier Transform Infra-red Spectroscope. These methods have been made inaccurate by the inability of such a method to accurately correct for the varied concentrations of other components of blood, for example, varying haemoglobin and fat, whose spectra overlay that of glucose (see also Clinical Chemistry Vol 35, No. 9 1854–1856). The light must enter and exit the prism at a precise angle and a fluid being examined must cover a constant surface area. These requirements as well as other variables such as temperature of the prism, make the application to a patient difficult and remote sensing, such as bed side monitoring, impossible. Also the "evanescent" wave produced by these A.T.R. systems penetrates less than 1 micron into the surrounding fluid making them impossible to use across a membrane or through skin for measuring blood sugar.

Methods have also been described which use such sources as $CO_2$ lasers as a source of discrete frequencies absorbed by the glucose molecule. These methods too cannot compensate for the varying concentrations of protein and fat and their effect on accuracy. They have the added disadvantage of requiring expensive and highly specialized bulky equipment and present some risk of burning the tissue being assayed.

It is, therefore, the object of the invention to provide a method for in vivo measurement of the concentration of a substance, e.g. glucose, in the blood by which method these difficulties are overcome and the measurement may be made using an inexpensive and portable system despite the varying concentrations of interfering substances such as other blood constituents including protein and fat.

This is obtained by a method for measuring the concentration of such a substance by measuring the absorption of selected wavelengths of infrared light, which method comprises the following steps:

selecting for each of the substance and the components a pair of different wavelengths of infrared light from the rage –40 μm one being a measuring wavelength at which the substance or component show a specific absorption and another being a reference wavelength at which the substance or component shows a low absorption, at least one wavelength being selected from the range 3–10 μm;

transmitting the selected wavelengths of infrared light to a surface part covering vascularized tissue of a person whose blood is being tested for its content of the substance;

placing at said surface part a detector detecting for each selected wavelength the absorbed amount of infrared radiation and giving of a computable electric signal expressing the measured absorption;

calculating the concentration of the substance taking into account the absorption caused by the interfering components, the calculation being performed by solving the equations:

$$w_1 = A_1[\text{substance}] + B_1[\text{component 1}] + C_1[\text{component 2}] + \ldots + N_1[\text{component } p]$$

$$w_2 = A_2[\text{substance}] + B_2[\text{component 1}] + C_2[\text{component 2}] + \ldots + N_2[\text{component } p]$$

$$w_n = A_n[\text{substance}] + B_n[\text{component 1}] + C_n[\text{component 2}] + \ldots + N_n[\text{component } p]$$

wherein w designates the absorption measured at each of the selected wavelengths each wavelength being designated by an index, the capitals $A_1, B_1, C_1, \ldots N_1$ to $A_n, B_n, C_n, \ldots N_n$ represents known absorption coefficients for the substance and the components at the respective selected wavelengths indicated by the index, and the figures in the brackets represent the concentrations of the substance and the components, respectively.

Known methods have concentrated on infrared spectroscopy in the near range from 0.700 to 1.5 μm as these wavelengths are capable of penetrating skin. Infrared spectroscopy in the far infrared range has been ignored as it has difficulty penetrating the skin and the weak measurement signals are heavily disturbed by absorption in the other blood constituents, water, protein and fat. However, the glucose molecule is more readily differentiated from the other components of the blood by its absorption spectrum in the far infrared range especially in the range 9–10 μm.

By the method according to the invention, profit is taken from the clearer "finger prints" of glucose in the far infrared range and the "noise" caused by the absorption in other blood components is compensated for by simultaneously measuring the concentrations of these components with separate reference sample wavelengths and compensating for the error in measurement these produce using experimentally derived constants.

A similar system has been used successfully in a commercial device called a Foss Milko-scan 104 A/B for the measurement of lactose in samples of dairy products (see U.S. Pat. No. 931,621). This system analyses milk using transmission through a sample in a test cuvette and measures the light absorbed using a thermopile light detector. Such a system is of course not applicable to in vivo measurement of glucose but serves to illustrate the efficacy of the principle.

The light may be transmitted to the tissue beneath the outer layer of skin and the absorption be measured by attenuated total reflection. By this invasive method and measurement the difficulty of the long wave infrared light, not penetrating the skin, is overcome, but the light may also non-invasively be transmitted to the outer side of the skin and the absorption may be measured by detecting the heat generated in the tissue, both these methods may be applied non-invasively to areas where the tissue is not covered by thick layers of epithelium such as inside the mouth.

The light transmitted to the tissue may be modulated and using different modulation frequencies for the different wavelengths of light used for measuring the concentration of different components the different pairs of wavelengths may be discriminated.

If, further, the different modulation frequencies are not harmonic the respective pairs of measuring and reference wavelengths may be discriminated even if they are transmitted simultaneously through the same transmission channel.

If the modulation of the measuring wavelength and the modulation of the reference wavelength is not in phase these measurements performed by each of these wavelengths may also be discriminated. By this method problems such as changing temperature or exposed surface areas may be overcome as both wavelengths, sample and reference, are exposed to the same conditions. The modulation may be provided by chopping the light.

The substance, the concentration of which is measured, is preferably glucose, but the method may also be used for measuring the concentration of $CO_2$ or ethanol in the blood, or the product of enzymic reaction of glucose, whereas the interfering components are the content of fat and protein. By measuring e.g. the ethanol content glucose may be seen as an interfering component.

The sample wavelength and the reference wavelength used are preferably for glucose 9.5 ±0.5 μm and 7.7 ±0.5 μm, respectively, or 3.47 ±0.5 μm and 2.96 ±0.5 μm, respectively, for fat 5.74 ±0.5 μm and 5.58 ±0.5 μm, respectively, or 3.513 ±0.5 μm and 3.57 ±0.5 μm, respectively, for protein 6.5 ±0.5 μm and 6.7 ±0.5 μm, respectively.

The invention also comprises an apparatus for carrying out the method this apparatus comprising:

a light aggregate able to provide selectable narrow bands of infrared light in the wavelength range of 1–40 μm;

light transmitting means for transmitting selected narrow bands of light to a measuring spot;

a detector detecting for each selected narrow band of infrared light the absorbed amount of infrared radiation at the measuring spot and giving of a computable electric signal expressing the measured absorption, a calculating unit for calculating the concentration of the substance taking into account the absorption caused by the interfering components by solving the equations:

$$w_1 = A_1[\text{substance}] + B_1[\text{component 1}] + C_1[\text{component 2}] + \ldots + N_1[\text{component } p]$$

$$w_2 = A_2[\text{substance}] + B_2[\text{component 1}] + C_2[\text{component 2}] + \ldots + N_2[\text{component } p]$$

$$w_n = A_n[\text{substance}] + B_n[\text{component 1}] + C_n[\text{component 2}] + \ldots + N_n[\text{component } p]$$

wherein w designates the absorption measured at each of the selected narrow bands of infrared light each band being designated by an index, the capitals $A_1, B_1, C_1, \ldots N_1$ to $A_n, B_n, C_n, \ldots N_n$ represents known absorption coefficients for the substance and the components at the respective selected wavelengths indicated by the indexes, which coefficients are stored in the calculating unit, and the figures in the brackets represent the concentrations of the substance and the components, respectively.

The apparatus may be designed as an apparatus using the method for measuring the glucose in a blood sample. Such an apparatus may be enclosed in a portable housing and may comprise an ATR device having an external surface on which a sample may be placed, and focusing means for transmitting light into the device and from the device to a the detector.

The light aggregate may comprise a wide-banded light source and a number of filters each transmitting one of the selected narrow bands, or it may comprise a number of surface emitting light emitting diodes each emitting infrared light of a chosen wavelength.

The light aggregate may further comprise means for focusing the light on an optical coupling means for the light transmitting means.

Further the light aggregate may comprise chopper means for chopping at preset chopping frequencies the light wave bands transmitted from the light aggregate. The chopper means may be mechanical in the shape of a rotating diaphragm with cutouts, or when the light aggregate comprises a number of light emitting diodes or semiconductor thermal source, an electronic circuit controlling the energizing of the light diodes or semi-conductor thermal sources.

The detector may in an invasive form comprise an optical needle probe ATR all having an input fibre and an output fibre and at the output fibre a light detector providing an output signal representing by an electrical signal the light absorption measured. The sensitivity of such an ATR cell may be enhanced by the addition of a thin metal coating to the outside of the cell such that it acts as a surface plasma resonance device.

The detector may have an overlying jacket of a glucose permeable membrane with a gap for fluid to collect to decrease the concentration of interfering substances further. The detector may also in its invasive form use the glucose permeable membrane jacketed ATR needle in conjunction with an enzyme and the method be used to measure glucose indirectly by means of measuring a product of enzymic reaction the infra-red absorption of which is measured in the same way as for glucose.

For non-invasive measurement the detector may comprise a pair of chambers having an open side placed against the skin on the measuring spot, and a pressure transducer measuring the pressure difference between the chambers and representing this differential pressure by an electric signal. The one chamber has at its side opposite the open side an inlet for infrared light radiation transmitted from the light aggregate. This construction makes it possible to detect the pressure produced in the chamber lying over the tissue which receives infrared light radiation when the absorption of this radiation is converted into heat in the tissue. Commonly made noises, e.g. those due to the pulse movement or due to pressure changes caused by common temperature variations in the skin, will automatically be rejected.

Such a method for use with ultra violet and visible light has been used for measurement of skin pigment and was published by Drs. Poulet and Chambron in The Journal of Medical and Biological Engineering and Computing, 1985, 23, 585–588. A similar method is described in European patent application No. 282,234. However, in the method we are using, light from the mid to far infra-red region is used which has not been described previously for an in vivo application. Also, in such previously described methods there is no method to solve the problem of interfering substances producing error in a quantitative assay, a problem overcome by this method.

Using such a two chamber detector receiving infrared light radiation in both its chambers makes it possible to measure the response produced by the light absorption of a sample wavelength against the response produced by the corresponding reference wavelength.

To compensate for noise caused by vibrations in the direction perpendicular to the diaphragm of the pressure transducer between the chambers a further transducer may be added to each chamber at the ends thereof and with their diaphragms in planes parallel with the diaphragm of the transducer between the chambers.

Another important source of disturbance is sweat secreted into the chambers. This may be eliminated by letting each chamber having an inlet for infrared radiation, communicate with a compartment containing a desiccant. In this way the water may be removed whereas the pressure provided in the chamber is maintained. This may also be achieved by means of a rigid but water permeable membrane to transport the water to the outside.

In the following, the invention will be explained with reference to the drawings, wherein FIG. 1 schematically shows a light aggregate for providing chopped infrared radiation of chosen wavelengths, FIG. 2 shows a diaphragm used for providing different chopping frequencies, FIG. 3 schematically shows a side elevation view of an optical fibre detector with ATR needle probe, FIG. 4 shows details of an ATR needle probe with an internal infusion canal, FIG. 5 shows details of an ATR needle probe attached to an infusion needle, FIG. 6 shows an optical fibre detector with an ATR needle probe with separate input fibres for each wavelength, FIG. 7 schematically shows an ATR needle probe inserted through the skin, FIG. 8 shows a detector detecting the heat response of the tissue beneath the skin when infrared radiation is transmitted to the skin, FIG. 9 shows another embodiment of a heat response detector, FIG. 10 shows a further development of the heat response detector in FIG. 9, FIG. 11 shows an electric coupling adding the outputs from the transducers of the detector in FIG. 10, FIG. 12 shows a heat response detector with all infrared radiation source in the form of emitting diodes carried on the detector, FIG. 13 shows seen from the bottom a double detector of the kind shown in FIG. 9, FIG. 14 schematically shows a view from the bottom of a triplicated detector of the kind shown in FIG. 9.

FIG. 15 shows another embodiment of the detector with a desiccant chamber,

FIG. 16 shows another embodiment of the detector with a water permeable membrane, FIG. 17 shows a further development of the ATR needle probe detector with a glucose permeable membrane, and FIG. 18 shows a detector detecting the transmission of light through a sample.

Figures 1A, 1B, 1C:
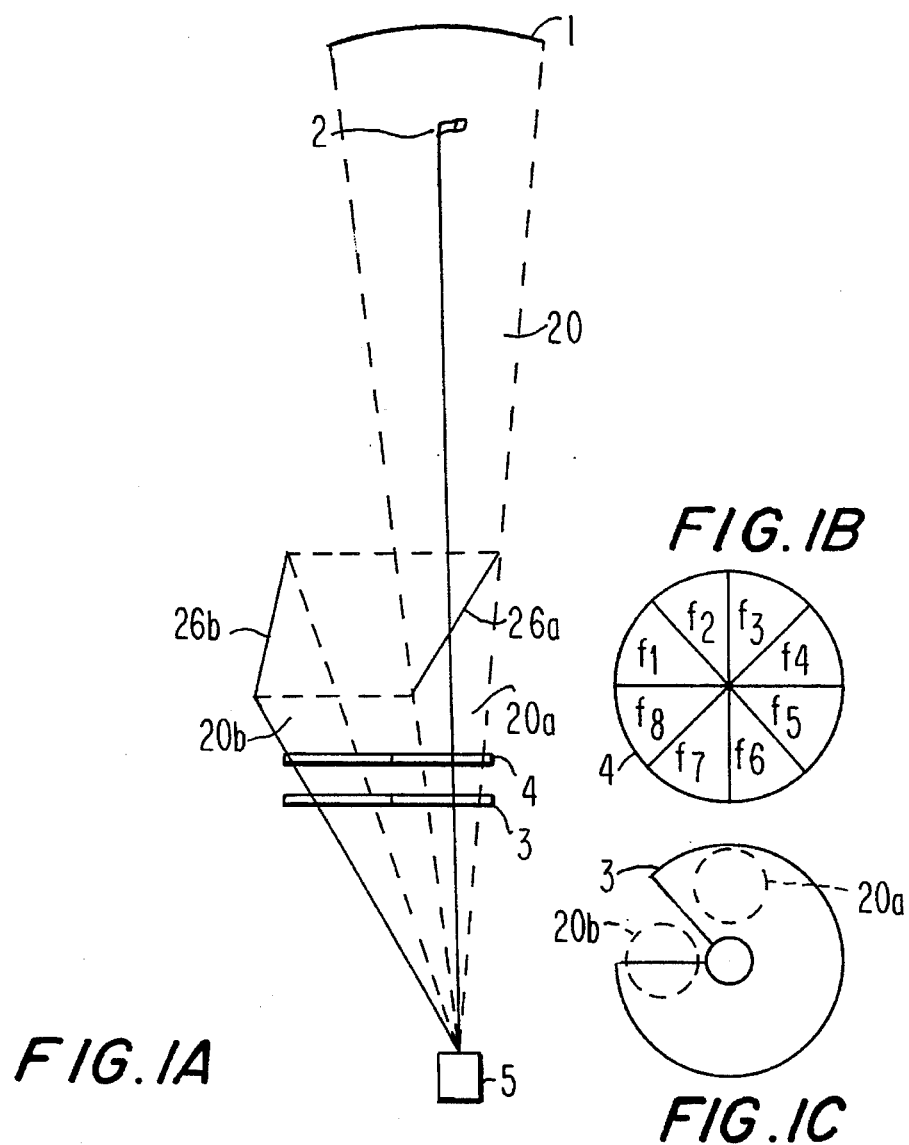

A light aggregate providing infrared light in selected wavelength bands is shown schematically in FIG. 1 wherein 2 is a source of wide-banded light and 1 is a concave mirror concentrating the light from the source 2 into a beam 20 of light which is passed through a beam splitting device comprising a semi-transparent reflecting surface 26a and a totally reflecting surface 26b. The two beams 20a, 20b of light provided in this way are transmitted through two different areas of a rotatable filter disc 4 which areas form filters $f_1$–$f_8$ for measuring wave bands and a reference wave bands, respectively.

In the path of the two beams 20a and 20b a rotary diaphragm 3 is placed having its center between the two beams and having a cut out sector. By rotating this diaphragm 3 the two light beams are chopped with the same frequency defined by the rotation speed of the diaphragm 3 and as indicated by the dotted circles the beams 20a and 20b are positioned such that the chopping of the respective beams will be out of phase. The aggregate is so designed that the two chopped beams are directed towards an optical coupling means 5 for coupling to the transmitting means transmitting the light to a sensor. The transmitting means may be an optical fibre or the transmission may take place directly through the air.

Figure 2:
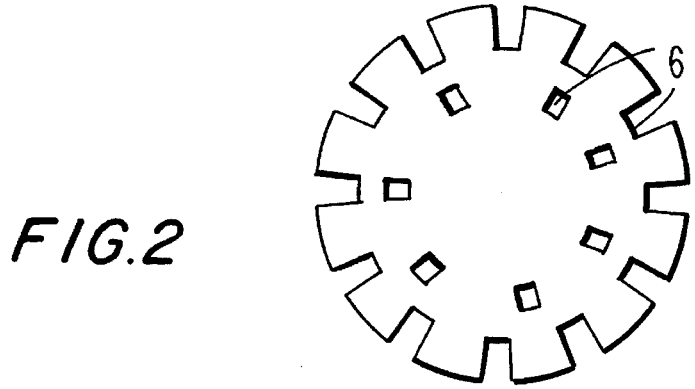

FIG. 2 shows another embodiment of the diaphragm 3. This diaphragm is designed to be rotated about a center placed at one side of the two beams and it has two sets of apertures 6 each set being placed on a circle concentric with the diaphragm, the numbers of apertures and the radii of the circles being different for the respective sets. The difference of the radii is equal to the distance between the two beams of infrared light. In this way the two light beams may be chopped at different frequencies.

Figure 3:
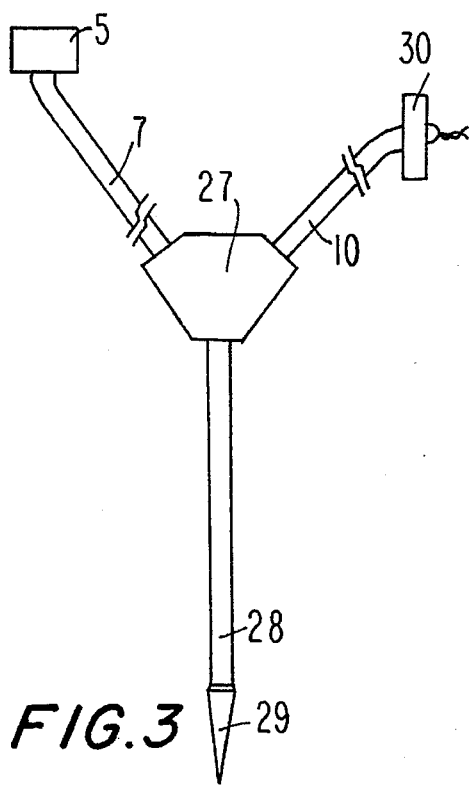
Figure 4:
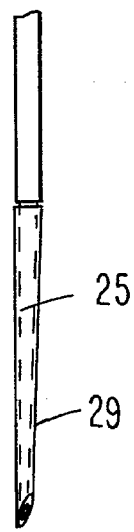
Figure 5:
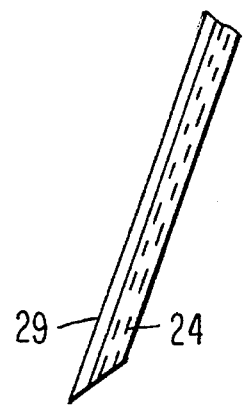

FIG. 3 schematically shows a detection device based on the attenuated total reflection (ATR) principle. From the coupling means 5 light is transmitted through an optical fibre 7, or fibre bundle through an optical device 27 directing the light frown the fibre 7 through another optical fibre 28 to a single ended ATR needle probe 29. The reflected light passes through the fibre 28 and is in the device 27 directed through the fibre 10 to a detector 30. As the active area of the ATR needle is the outer surface a further embodiment of this device includes the ATR needle 29 having a central canal as illustrated in FIG. 4. FIG. 5 shows a similar embodiment with the ATR needle 29 attached to a metal needle 24 for infusion of fluids.

Figure 6:
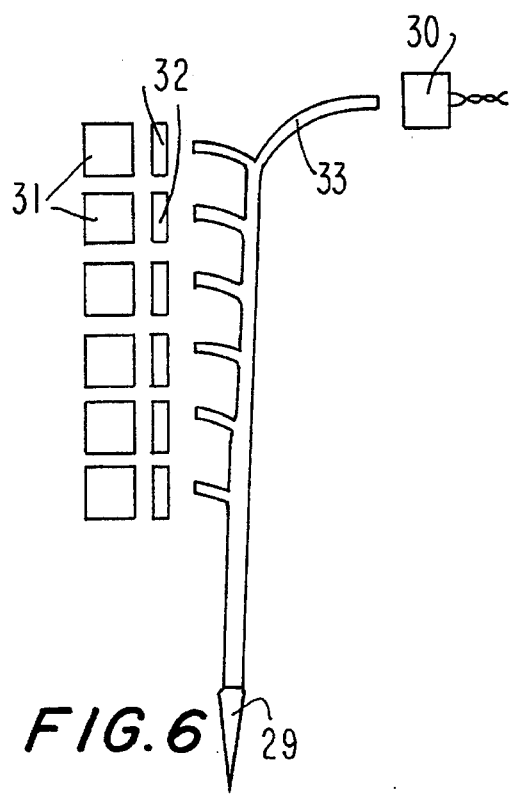

In FIG. 6 an input fibre to the ATR-needle 29 comprises a number of fibres each connected to its individual semiconductor thermal device 31. Monochromatic IR filters 32 between each thermal device 31 and its corresponding fibre allow each fibre in the bundle to carry a specific light wave band. A specific light wave band for the fibre may also be produced using a single thermal device 31 and a filter wheel. In another embodiment not shown the devices 31 may be narrow band light emitting diodes each emitting infrared light in a chosen band. In this case no monochromatic IR filters would be needed. The reflected light passes back up the core fibre of the bundle 33 to the detector 30.

Figure 7:
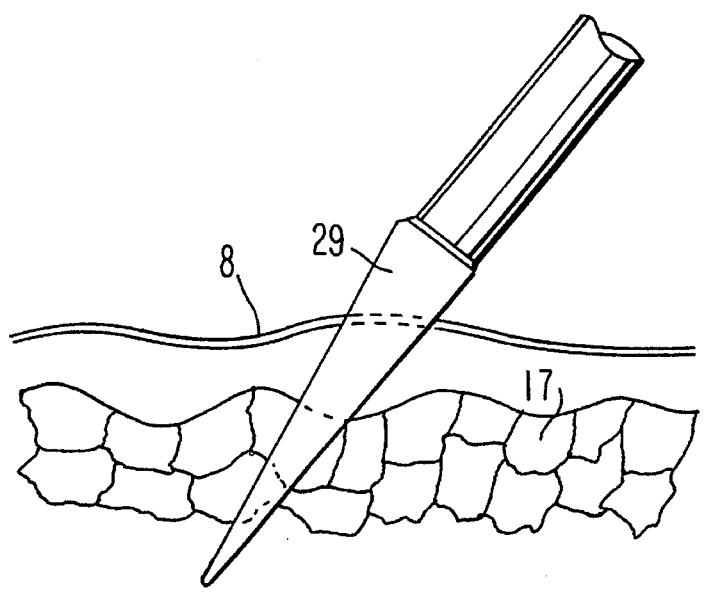

The ATR needle 29 is inserted through the skin 8 into the subcutaneous tissue 17 as shown in FIG. 7. As shown in FIGS. 4 and 5, the ATR-needle probe may have a canal for infusion of fluid or it may be attached to a needle for subcutaneous infusion of a fluid, e.g. insulin.

Figure 8:
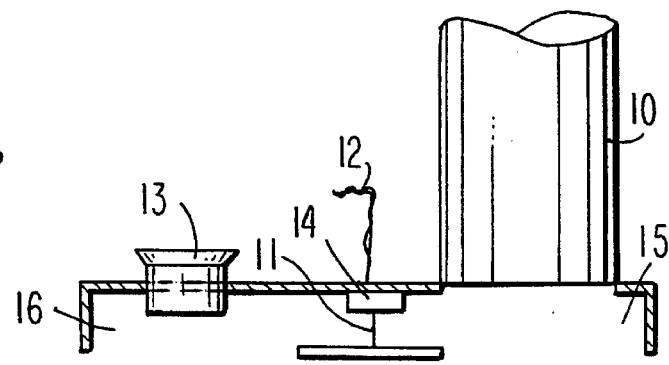

FIG. 8 shows a detector which may be used for non-invasive detection of the absorption of infrared light transmitted to the skin. The detector comprises a sensing chamber 15 and a reference chamber 16 and a differential pressure transducer 14 measuring the pressure difference between the chambers 15 and 16 and giving off an electric signal through leads 12, this signal being representative of the pressure difference. The reference chamber 16 has a screw 13 for adjusting the volume of the response by damping background noise.

Infrared light is transmitted from the light aggregate to the sensing chamber through an optical fibre 10 and will pass across the air space in the sensing chamber and into the skin.

As the beam of radiation passes through the skin into the underlying tissue certain molecules absorb radiation of specific wavelengths and convert it into heat. This heat then diffuses to the surface and heats the air in the chamber producing a pressure wave. The light which is pulsed stimulates cycles of heating and subsequent cooling in the skin which in turn produces pressure waves in the chamber at the same frequency as the pulses of light. This is detected by the pressure transducer 14 and is converted into an electrical signal. The amplitude of the electrical signal is in proportion to the amount of heat produced which is proportional to the number of molecules or the concentration of that substance.

Pressure waves in the detector may be produced by sound waves arising from the body, and are therefore noise, reach both chambers and the pressure changes in both chambers therefore being equal do not move the transducer diaphragm placed between the chambers.

As the heat from the deeper layers will take longer to diffuse to the surface the delay in the signal can be used to relatively select out an area of the deeper layers of skin. In this way the concentration of the blood sugar in the vessels of the dermis can be measured.

Figure 9:
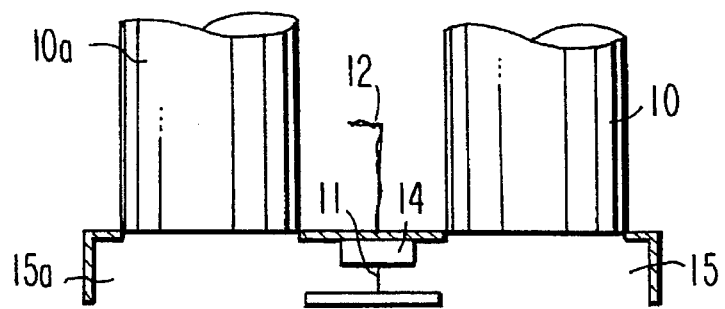

In another embodiment shown in FIG. 9 infrared light is transmitted to both of the chambers of the detector, light of the sample wavelength being transmitted to one chamber 15 and light of the reference light wavelength being transmitted to the other 15a. The transducer 14 measures the pressure difference between the two chambers 15 and 15a and the response signal is led to a measuring device by leads 12.

By adjusting the light radiation of the reference and the sample beam such that the pressure difference between the two chambers is low when the concentration of the measured substance in the skin is low much improved sensitivity of the pressure transducer can be obtained by increasing the sensitivity of the pressure difference transducer.

Figure 10:
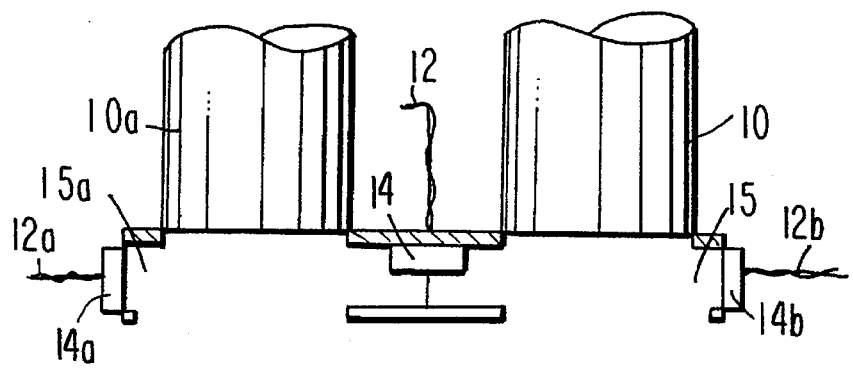

In a further development of the above detector as shown in FIG. 10 two further pressure transducers 14a and 14b are added, at the end of the chamber lying opposite the transducer 14 between the chambers 15 and 15a and with their diaphragms lying in planes parallel with the plane of the diaphragm of the transducer 14. As the two further transducers 14a and 14b face each other their signals are opposite when their diaphragms are relatively moved due to movement of the total device in a direction perpendicular to the planes of the diaphragms.

Figure 11:
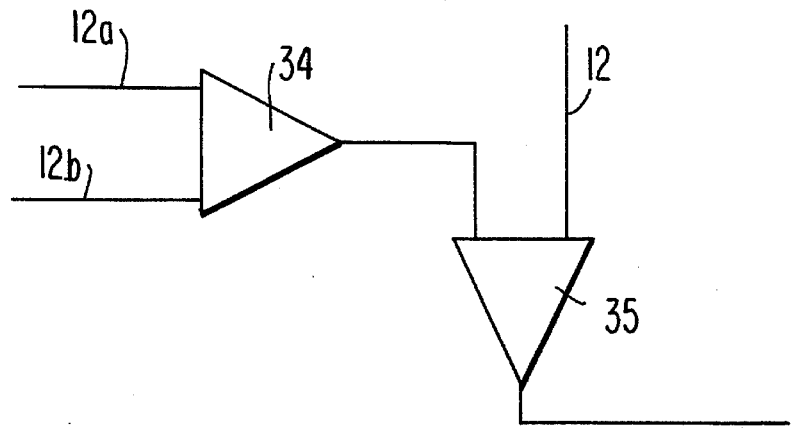

The signals from the transducers 14a and 14b are amplified and balanced and electrically added to the signal from the differential pressure transducer 14 as shown by the electrical diagram in FIG. 11. One of the signals from leads 12a and 12b is inverted and added to the other in the amplifier 34, and the added signal is added to the differential signal on the leads 12, amplified in an amplifier 35. By so doing the response in the chambers is increased and the noise due to horizontal vibration reduced.

Figure 12:
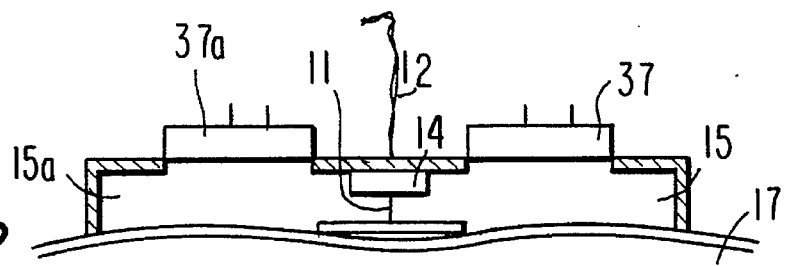

In the above embodiments the light is transmitted from a light aggregate to the detector through optical fibres or other kinds of light transmitting means. In another embodiment shown in FIG. 12 the light is generated in the detector by surface emitting light diodes 37 and 37a emitting infrared light at the sample wavelength and the reference wavelength, respectively. From the light diodes 37 and 37a light passes over the space of the chambers 15 and 15a into the tissue 17. The pressure change produced is measured by the pressure transducer 14 and the response signal is carried by the leads 12 to a measuring and computing device.

The use of light emitting diodes will make the detector more mobile as only electric connections to controlling means and to the measuring and calculating device will be necessary. Less mobile is a detector which further has to be connected to a light aggregate through an optical fibre. Embodiments using a conventional optical transmission will be immobile to an extent making it necessary to bring the measuring object to the device rather than bringing the detector to the sampling spot of the patient.

With the above thermal detectors the relation between the response of the tissue to a sample wavelength and to its reference wavelength may be measured. The response may be measured for all the sample wavelengths and the reference wavelengths in sequence or overlapping in a way making it possible to discriminate the individual relations.

Figure 13:
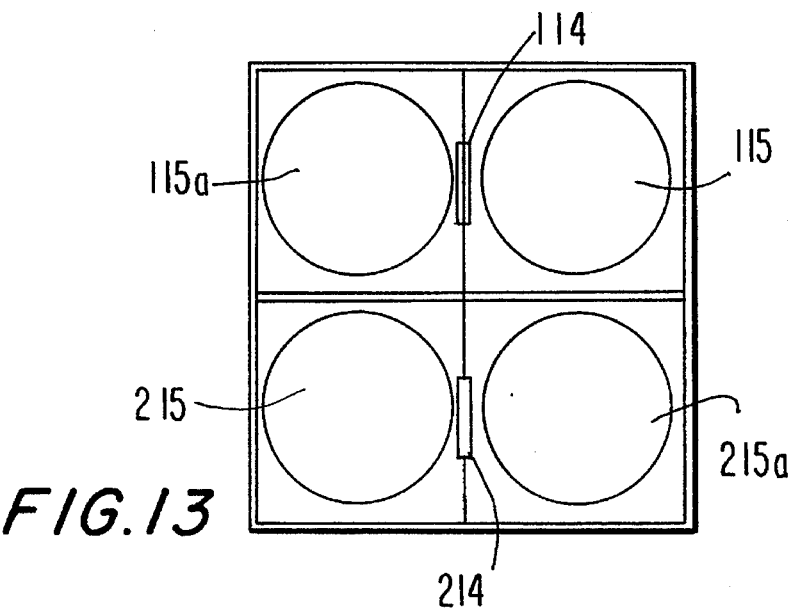

Another way of performing a simultaneous measurement at two wavelengths, e.g. a sample wavelength and a reference wavelength and cancelling the effect of "lateral" movement is using a detector comprising a doubling of the device according to FIG. 9. In this way four chambers 115, 115a, 215 and 215a are provided as seen in FIG. 13 showing the double detector seen from the bottom. The two sets of sample and reference wavelengths are transmitted to the respective detector units through optical. fibres and the response of the tissue to the two sets of wavelengths is measured by transducers 114 and 214. The detector units being oriented oppositely implies that signals from the two transducers 114 and 214 clue to longitudinal vibrations could be added to each other and balanced out.

Figure 14:
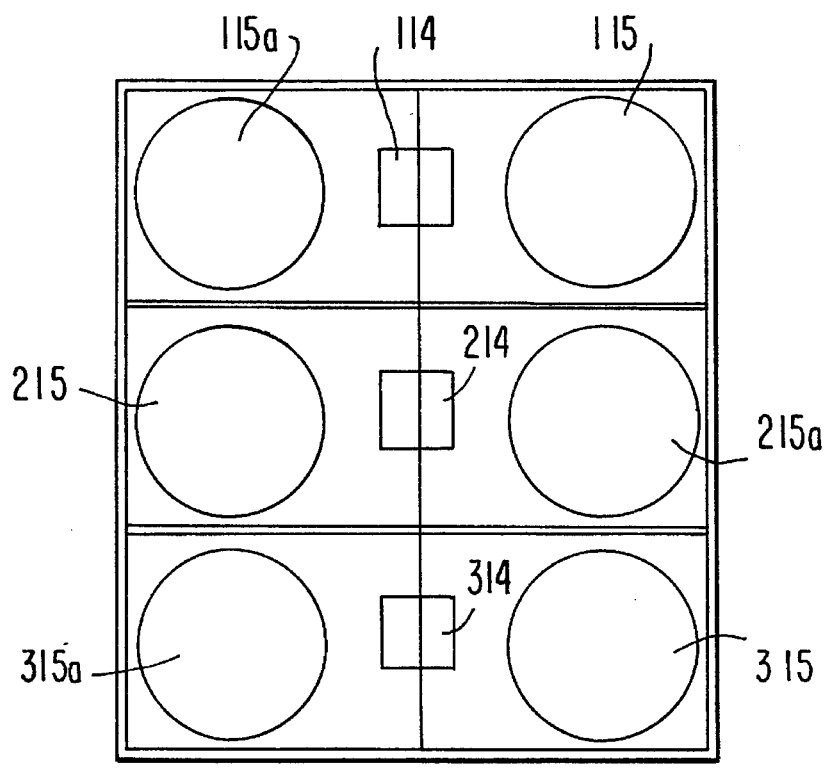

In the same way the detector of FIGS. 9 to 12 may be triplicated to measure the relations of the responses to three pairs of wavelengths that are three pairs of sample wavelengths and reference wavelengths thus decreasing measuring time and ·eliminating noise from horizontal vibration. Such a triplicated detector is schematically shown seen from the bottom in FIG. 14. The sample and reference chambers have the reference numbers 115, 215, 315 and 115a, 215a, 315a, respectively, infrared light being transmitted to each chamber through optical fibres. Each transmitting fibre carries an individual wavelength.

As collection of condensing water especially in a chamber to which infrared radiation is transmitted in a thermal detector of the kind described impairs the measurement precautions should be taken to remove water and water vapor from such chambers. This may be done as sketched in FIG. 15 by providing compartments 38 communicating with the chamber to be dehydrated and place a desiccant in this compartment. Another possibility is as sketched in FIG. 16 to provide the chambers 15, 15a with water permeable membranes 39 between the inner of the chambers 15, 15a, respectively, and the atmosphere.

The efficiency of the ATR needle probe 29 shown in FIG. 3 can be further enhanced by the addition of an extremely thin metal coating to be outside of the ATR needle (not shown) so as to make it act as a surface plasma resonance device. FIG. 17 illustrates a further embodiment of the ATR needle shown in FIG. 3. The probe is jacketed by a glucose permeable membrane 40 with a space below 41 for fluid to collect between the membrane 40 and the ATR needle 29. Furthermore, the membrane may incorporate an enzyme (not shown) and ATR needle detector used to measure a product of that enzymic reaction in the fluid space 41.

FIG. 18 illustrates a further detector whereby the light is transmitted from a coupling device (not shown) down an input optical fibre 7, through a lens (not shown) and reflected by mirror 42a across a gap 43 into which tissue fluid may freely enter and the transmitted light is reflected by mirror 42b into the output optical fibre 10 and to a light detector (not shown).

Figure 19:
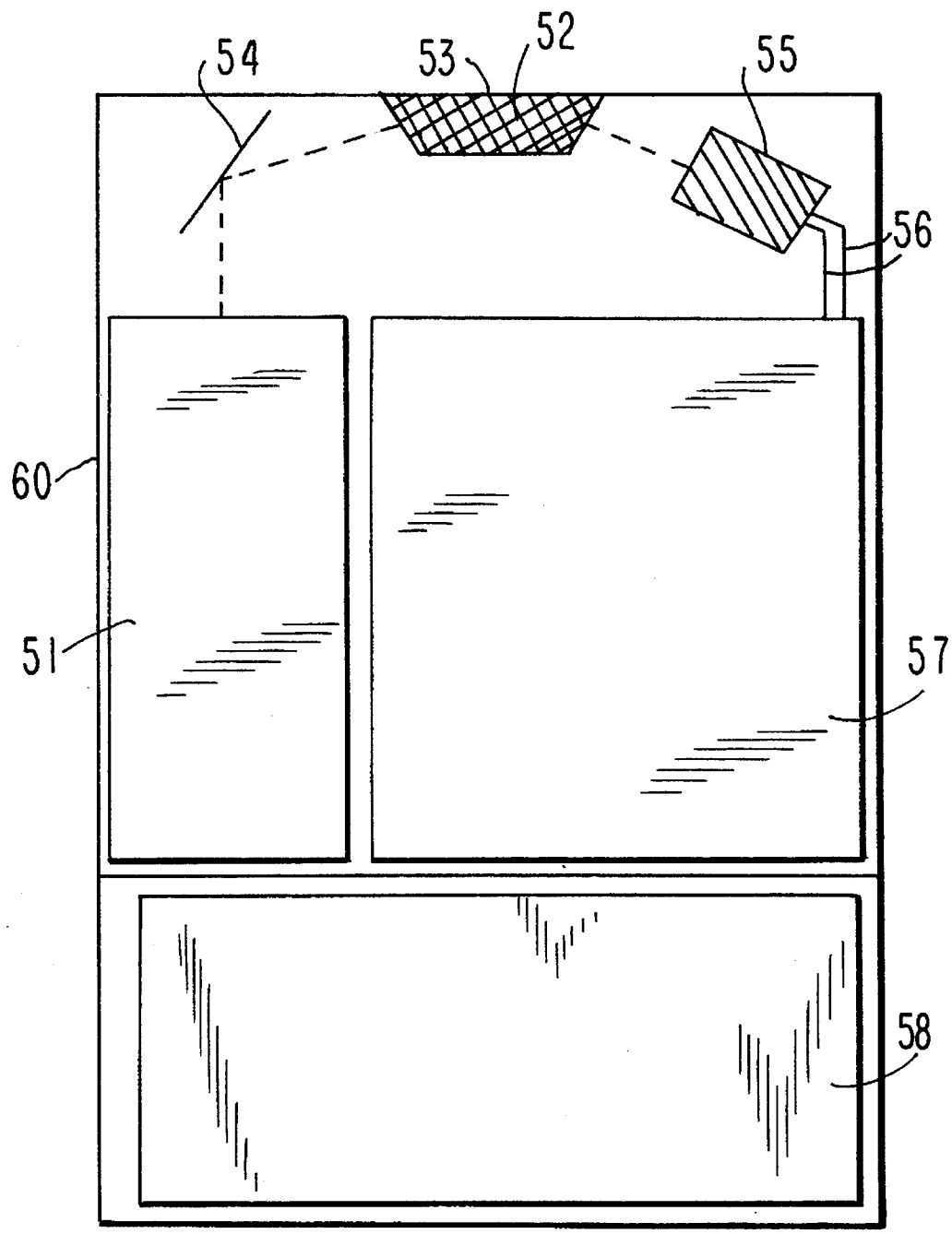
FIG. 19 shows schematically a portable blood glucose measuring apparatus

FIG. 19 shows a portable apparatus for in vitro measuring the glucose content in a blood sample.

The apparatus is confined by a housing 60 and comprises a light source 51 from which light of the chosen wavelengths are led to an ATR crystal 52 having a surface 53, which is accessible from the outside of the housing and acts as the window onto which the sample should be placed.

The light from the light source 51 is by a mirror 54 led to the ATR crystal, and in the beam leaving the crystal 52 a detector 55 is placed, which detector converts the light signals to electric signals, which through electric leads 56 are led to a computer 57, which on the basis of the electric signals calculates the wanted concentration. The results may be displayed on a not shown display. To supply the light source and the computer a power supply 58 is provided.

I claim:

1. A method for in vivo measurement of a substance's concentration in blood, despite varying concentrations of interfering components, by measuring absorption of selected wavelengths of infrared light, the method comprising, selecting for each of the substance and the components a pair of different wavelengths of infrared light from the range of 1–40 µm, one being a measuring wavelength at which the substance or component show a specific absorption and another being a reference wavelength at which the substance or component shows a low absorption, at least one wavelength being selected from a range of 3–10 µm;

transmitting the selected wavelengths of infrared light to a surface part covering vascularized tissue of a person whose blood is being tested for its concentration of the substance;

placing at said surface part a detector detecting for each selected wavelength the absorbed amount of infrared radiation and giving of a computable electric signal expressing the measured absorption;

calculating the concentrations of the interfering components, and calculating the concentration of the substance using the absorption measurement at the substance measuring and reference wavelengths taking into account the absorption caused by the interfering components at the measuring and reference wavelengths for this substance, the interfering absorption being calculated taking into account the measured concentrations of the interfering components and experimentally derived constants.

2. A method according to claim 1, wherein the substance the concentration of which is measured is glucose and the interfering components are fat, protein and water.

3. A method according to claim 1, wherein the substance the concentration of which is measured is $CO_2$ and the interfering components are glucose, fat, protein and water.

4. A method according to claim 1, wherein the substance the concentration of which is measured is ethanol and the interfering components are glucose, fat, protein and water.

5. A method according to claim 4, wherein the sample wavelength and the reference wavelength used for glucose are 9.5 ±0.5 μm and 7.7 ±0.5 μm, respectively.

6. A method according to claim 4, wherein the sample wavelength and the reference used for glucose are 3.47 ±0.5 μm and 2.96 ±0.5 μm, respectively.

7. A method according to 4, wherein the sample wavelength and the reference wavelength for fat are 5.74 ±0.5 μm and 5.58 ±0.5 μm, respectively.

8. A method according to claim 4, wherein the sample wavelength and the reference wavelength for fat are 3.513 ±0.5 μm and 3.57 ±0.5 μm, respectively.

9. A method according to claim 4, wherein the sample wavelength and the reference wavelength for protein are 6.5 ±0.5 μm and 6.7 ±0.5 μm, respectively.

10. A method according to claim 1, wherein the light is transmitted to the tissue and the light absorption is measured by attenuated total reflection transcutaneously, i.e. invasively or non-invasively.

11. A method according to claim 1, wherein the light is transmitted to the outer side of the surface part and the absorption is measured by detecting the heat generated in the tissue beneath the skin.

12. An apparatus for measurement of the concentration of a substance in blood despite varying concentrations of interfering components by measuring the absorption of selected wavelengths of infrared light, this apparatus comprising a light aggregate able to provide selectable narrow bands of infrared light in the wavelength range of 1–40 μm;

light transmitting means for transmitting selected narrow bands of light to a measuring spot;

a detector detecting for each selected narrow band of infrared light the absorbed amount of infrared radiation at the measuring spot and giving of a computable electric signal expressing the measured absorption, a calculating unit for calculating the concentration of the substance measuring and reference wavelengths taking into account the absorption caused by the interfering components at the measuring and reference wavelengths for this substance, the interfering absorption being calculated taking into account the measured concentrations of the interfering components and experimentally derived constants.

13. An apparatus according to claim 12 enclosed in a portable housing and comprising an ATR device with an external surface on which a sample may be placed, and focusing means for transmitting light into the device and from the device to a the detector.

14. An apparatus according to claim 13 where the light aggregate comprises a wide-banded light source and a number of filters each transmitting one of the selected narrow light bands.

15. An apparatus according to claim 13, wherein the light aggregate comprises a number of surface emitting light diodes each emitting infrared light of a chosen wavelength.

16. An apparatus according to claim 13, wherein the light aggregate comprises means for focusing the light on an optical coupling means for the light transmitting means.

17. An apparatus according to claim 16, wherein the chopper means is provided as an electronic circuit controlling the energizing of light diodes or semiconductor sources.

18. An apparatus according to claim 13, wherein the light aggregate comprises chopper means for chopping at preset chopping frequencies the light wave lengths transmitted from the light aggregate.

19. An apparatus according to claim 18, wherein the chopper means is a rotating diaphragm with cut-outs.

20. An apparatus according to claim 13, comprising an optical needle probe ATR cell having an input fibre and an output fibre, the detector being provided at the output fibre.

21. An apparatus according to claim 20, wherein the ATR needle probe cell is coated with a metal such that it acts as a surface plasma resonance device.

22. An apparatus according to claim 21, wherein the metal coated ATR needle probe is jacketed by a cellulose permeable membrane with a gap between the membrane and the probe.

23. An apparatus according to claim 22, wherein the membrane has a glucose specific enzyme or system of enzymes and the ATR prove is used to measure the product of enzymic reaction of the glucose molecule.

24. An apparatus according to claim 12, wherein the detector comprises a first and a second chamber each having an open side placed against the skin at the measuring spot, and a pressure transducer comprising a diaphragm and measuring the pressure difference between the chambers representing this differential pressure by an electric signal.

25. An apparatus according to claim 24, wherein the first chamber at a side opposite the open side has an inlet for infrared radiation transmitted from the light aggregate.

26. An apparatus according to claim 24, wherein both chambers have at a side opposite the open side inlets for infrared radiation transmitted for the light aggregate.

27. An apparatus according to claim 24, wherein a further transducer is added to each chamber at an end thereof and with a diaphragm lying in a plane parallel with the plane of the diaphragm of the transducer between the chambers.

28. An apparatus according to claim 27, wherein each chamber has an inlet for infrared radiation communicates with a compartment containing a desiccant.

29. An apparatus according to claim 27, wherein each chamber has an inlet for infrared radiation each chamber having a wall with a rigid water permeable membrane.

* * * * *